United States Patent
Camprasse et al.

(10) Patent No.: US 10,342,895 B2
(45) Date of Patent: Jul. 9, 2019

(54) PULVERULENT SEMISYNTHETIC MATERIAL OBTAINED BY MODIFYING THE COMPOSITION OF A NATURAL MARINE BIOMATERIAL, METHOD OF MANUFACTURE THEREOF, AND APPLICATIONS THEREOF

(71) Applicant: MBP (MAURITIUS) LTD, Port Louis (MU)

(72) Inventors: Georges Camprasse, Arnage (FR); Serge Camprasse, La Fleche (FR)

(73) Assignee: MBP (MAURITIUS) LTD, Port Louis (MU)

( * ) Notice: Subject to any disclaimer, the term of this patent is extended or adjusted under 35 U.S.C. 154(b) by 73 days.

(21) Appl. No.: 15/187,964

(22) Filed: Jun. 21, 2016

(65) Prior Publication Data

US 2016/0375173 A1 Dec. 29, 2016

Related U.S. Application Data

(60) Provisional application No. 62/183,211, filed on Jun. 23, 2015.

(51) Int. Cl.
| | |
|---|---|
| A61L 27/02 | (2006.01) |
| A61L 27/14 | (2006.01) |
| A61L 27/36 | (2006.01) |
| A61L 27/58 | (2006.01) |
| A61L 17/08 | (2006.01) |
| A61L 24/00 | (2006.01) |
| A61L 24/02 | (2006.01) |
| A61L 17/06 | (2006.01) |

(52) U.S. Cl.
CPC ............. *A61L 27/025* (2013.01); *A61L 17/06* (2013.01); *A61L 17/08* (2013.01); *A61L 24/0005* (2013.01); *A61L 24/0042* (2013.01); *A61L 24/02* (2013.01); *A61L 27/14* (2013.01); *A61L 27/3604* (2013.01); *A61L 27/58* (2013.01); *A61L 2300/412* (2013.01); *A61L 2300/604* (2013.01); *A61L 2430/02* (2013.01)

(58) Field of Classification Search
None
See application file for complete search history.

(56) References Cited

FOREIGN PATENT DOCUMENTS

| WO | 9014111 | 11/1990 |
| WO | 9530426 | 11/1995 |

*Primary Examiner* — Mina Haghighatian
*Assistant Examiner* — Luke E Karpinski
(74) *Attorney, Agent, or Firm* — Maier & Maier, PLLC

(57) ABSTRACT

A pulverulent semisynthetic material, derived from a natural marine biomaterial, namely the aragonitic inner layer of the shell of bivalve molluscs selected from the group including Pinctadines, notably *Pinctada maxima, margaritifera*, and Tridacnes, notably *Tridacnagigas, maxima, derasa, tevaroa, squamosa, crocea, Hippopushippopus, Hippopusporcelanus*, in pulverulent form, with addition of insoluble and soluble biopolymers and calcium carbonate transformed by carbonation; it also relates to the method of preparation thereof and to the uses thereof.

7 Claims, 1 Drawing Sheet

Figure 1:
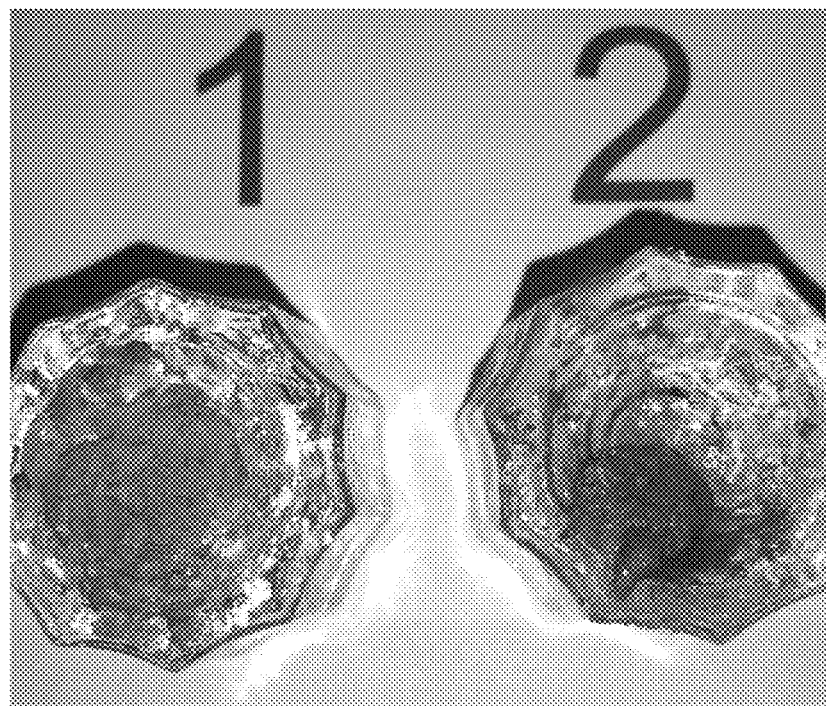

PULVERULENT SEMISYNTHETIC MATERIAL OBTAINED BY MODIFYING THE COMPOSITION OF A NATURAL MARINE BIOMATERIAL, METHOD OF MANUFACTURE THEREOF, AND APPLICATIONS THEREOF

FIELD OF THE INVENTION

The present invention relates to a pulverulent semisynthetic bioabsorbable material, obtained from a natural marine biomaterial derived from the shell of bivalve molluscs such as the Pinctadines (oysters) in general and notably *Pinctada maxima, margaritifera*, and the Tridacnes (giant clams): *Tridacna gigas, maxima, derasa, tevaroa, squamosa, crocea, Hippopus hippopus, Hippopus porcelanus*.

CONTEXT OF THE INVENTION

Generally the materials used for filling losses of bone substance of traumatic, tumoral, dystrophic or degenerative origin are calcium phosphate cements, bio-copolymers, and materials of animal or human origin.

For sealing prostheses, only polymethylmethacrylate (PMMA) is used, optionally combined with antibiotics, an initiator, an activator, an opacifier or a colorant. Endoprostheses are generally sealed with PMMA cements, the drawbacks of which are well known, in particular the exothermic reaction produced during polymerization of the cement, the resulting osteocyte necrosis, shrinkage of the cement over time and ageing thereof, which cause mobility of the prosthesis and the need to repeat it within 10 to 15 years after surgery, in most cases.

All these materials are biocompatible, and some of them, such as the calcium phosphate cements, claim osteoconduction properties; few are bioactive, the majority being inert.

The injectable cements consist of a mineral phase and a liquid phase, which may be phosphoric acid, an aqueous solution or gel of HPMC, stoichiometric water of 0.1 mole, sulphuric acid, or citric acid.

The biomaterials, synthetic or of bovine origin, used as bone substitutes, present essentially osteoconduction properties and generally are not completely bioabsorbable.

For some of them, notably the polymers, it is found that there is release of degradation products, which may in the long term have harmful effects on the surrounding or systemic diseased tissues. This bioabsorption is patient-dependent.

Moreover, nearly all of the bone substitutes are not bioactive; this necessitates combining them with collagen of animal origin, or with other substances which, being bioabsorbed, induce a major inflammatory reaction in the recipient, greater than and different from the physiological reaction.

The major drawback of bone substitutes in the form of powder or granules is that during use, whether with autologous blood, saline solution or any other liquid carrier, they do not form a "coagulum" having adhesive and plastic properties promoting their cohesion and maintenance on and in the site.

It is known that human bone consists of 43% of inorganic components, 32% of organic components and 25% water. The organic component consists of 90% of collagen proteins—including 97% of type I, of type III, IV and V collagen—as well as 10% of non-collagen proteins represented by osteocalcin, osteonectin, osteopontin, bone sialoprotein, proteoglycans, fibronectin, growth factors and morphogenic proteins. These non-collagen proteins play an essential role in the processes of osteogenesis and repair of damaged tissues.

The inorganic fraction largely consists of hydroxyapatite in the form of crystals of calcium phosphate; this fraction also contains other minerals such as sodium, potassium, copper, zinc, strontium, fluorine, aluminium, and silicon in very small amounts. All these elements play an important role in cellular metabolism as well as in healing and bone regeneration.

Investigation of the architecture and composition of the shell of the bivalve molluscs, such as Pinctadines in general and notably *Pinctada maxima, margaritifera*, and the Tridacnes, notably *Tridacna gigas, maxima, derasa, tevaroa, squamosa, crocea, Hippopus hippopus, Hippopus porcelanus*, has shown that it comprises a nacreous inner layer, made up of 3 to 5% of an organic fraction, itself consisting of collagen proteins and non-collagen proteins, essentially insoluble and soluble biopolymers. The nacreous inner layer also contains an inorganic fraction representing 95 to 97%, consisting essentially of calcium carbonate, minerals and metal ions, as well as 3% water. This investigation of the architecture of the shell of the molluscs to which the invention relates also shows that it consists of a calcitic outer layer, structurally different from the aragonitic inner layer, but also containing an organic fraction made up of insoluble and soluble biopolymers.

Several publications have demonstrated the osteoinduction and osteoconduction properties of the natural biomaterial derived from the aragonitic layer of the marine molluscs mentioned above.

These properties result from the presence of biopolymers contained in the organic fraction, in which structural proteins similar to those that contribute to the architecture of organs such as the teeth, bones, skin, muscles, mucosae, etc. have been identified. Functional proteins similar to those that are involved in metabolic and biochemical processes (enzymology, immunology, membrane receptors, signal molecules, etc.) are also present. The collagens are particularly represented among these structural proteins: thus, type I, II, III and related collagens have been identified.

Apart from the free amino acids, the presence of proteoglycans (carbohydrates bound to small peptides), and of glycoproteins (association of collagen and carbohydrates) including glycoproteins of low molecular weight, generally regarded as growth factors related to BMP, TNF β, TGF β, PGF, etc., has been identified.

Moreover, it is known that certain non-collagen molecules have a fundamental role in the physiological healing process and in cell and tissue regeneration.

The properties of healing, regeneration, angiogenesis and osteoinduction of the organo-mineral complex of the inner layer of the shell of the aforementioned molluscs, properties linked to the presence of these various collagens and growth factors, have been demonstrated in vitro and in vivo.

If we compare the physicochemical composition of bone tissue and that of aragonite of the shells of the molluscs in question, we note great similarity of the organic components present at a percentage of 32% in bone tissue and from 3 to 5% in aragonite. The mineral phases, 43% for bone, essentially calcium phosphate, represent in aragonite 95 to 97% in the form of calcium carbonate; the proportions of the other minerals are very similar.

Taking into account the role of the biopolymers contained in the organic fraction of the natural marine biomaterial, the inventors found it pertinent to modify its composition by increasing the proportion of these biopolymers in the composition of a novel semisynthetic hybrid biomaterial.

It is known that the organic fraction of the aragonitic inner layer and calcitic outer layer of the shells of the molluscs in question contains soluble, diffusible molecules, having osteogenic properties involved in the mineralization and growth of calcified tissues. The presence of insoluble structural proteins in the peri-crystalline and interlamellar envelopes of aragonite has also been demonstrated.

Moreover, the molecules contained in the organic fraction of the calcitic outer layer of the shell are similar to those contained in the aragonitic inner layer of the shell of the molluscs to which the invention relates.

That is why it seemed pertinent to extract and concentrate not only the organic molecules closely linked to the biocrystals and to the intercrystalline lamellae of which the aragonite of the nacreous tests is constituted, but also those contained in the calcitic outer layer of the shells of the molluscs in question.

Extraction of the biopolymers of the organic fractions of the biomaterial has the aim of providing soluble and insoluble molecules. The objective is to be able to increase, by supplementing with extracted insoluble and soluble biopolymers, the organic-inorganic structural ratio, in order to optimize the properties of cell and tissue regeneration, healing, osteoinduction, and angiogenesis of the biomaterial thus obtained.

Thus, the present inventors found that it is possible, starting from the shell of a mollusc selected from *Tridacna maxima, Tridacna gigas, Tridacna derasa, Tridacna tevaroa, Tridacna squamosa, Tridacna crocea, Hippopus hippopus, Hippopus porcelanus, Pinctada maxima, Pinctada margaritifera*, and other Pinctadines, to obtain a material that meets these requirements by adding to it both soluble and insoluble biopolymers and calcium carbonate transformed by carbonation.

Thus modified, the novel pulverulent semisynthetic bioabsorbable material according to the invention is intended for manufacturing, for example, bone substitutes, injectable cements or cements for sealing endoprostheses, or for making bioabsorbable osteosynthesis devices and moulded implants.

Thus, according to a first aspect, the invention relates to a pulverulent semisynthetic material, derived from a natural marine biomaterial, with addition of insoluble and soluble biopolymers and calcium carbonate transformed by carbonation.

The invention also relates to a method for preparing this semisynthetic material.

It also relates to a composition comprising the soluble and insoluble biopolymers or calcium carbonate transformed by carbonation employed in the semisynthetic material.

It finally relates to the use of the semisynthetic material or of the composition for manufacturing for example bone substitutes, injectable cements or cements for sealing endoprostheses, or else for making bioabsorbable osteosynthesis devices and moulded implants.

DETAILED DESCRIPTION OF THE INVENTION

According to a first aspect, the invention relates to a pulverulent semisynthetic material, derived from a natural marine biomaterial, with addition of insoluble and soluble biopolymers and calcium carbonate transformed by carbonation.

The material according to the invention is derived from a natural marine biomaterial, namely the aragonitic inner layer of the shell of bivalve molluscs selected from the group comprising Pinctadines, notably *Pinctada maxima, margaritifera*, and Tridacnes, notably *Tridacna gigas, maxima, derasa, tevaroa, squamosa, crocea, Hippopus hippopus, Hippopus porcelanus*, said aragonitic layer being in pulverulent form.

The pulverulent semisynthetic material according to the invention is bioabsorbable.

According to one embodiment, the granulometry is from 5 nm to 100 μm, preferably from 20 nm to 50 μm, even more preferably from 50 nm to 20 μm.

The soluble and insoluble biopolymers are extracted from the aragonitic inner layer and/or from the calcitic outer layer of the shell of the bivalve molluscs selected from the group comprising Pinctadines, notably *Pinctada maxima, margaritifera*, and Tridacnes, notably *Tridacna gigas, maxima, derasa, tevaroa, squamosa, crocea, Hippopus hippopus, Hippopus porcelanus*.

A method for extracting these polymers is described hereunder.

According to a particular embodiment, the extracted soluble biopolymers and insoluble biopolymers are added in a ratio of soluble biopolymers to insoluble biopolymers corresponding to that existing in the starting biomaterial.

The calcium carbonate transformed by carbonation employed in the semisynthetic material of the invention is derived from a natural terrestrial, natural marine or precipitated calcium carbonate, or from the inorganic fraction of the aragonitic layer after extraction of the insoluble and soluble biopolymers, which was transformed by carbonation. It is known that calcium carbonate, crystallized in the orthorhombic or rhombohedral system, when submitted to thermal treatment between 800 and 1100° C., presents, through thermolysis and oxidation, new properties that are reflected in considerable adhesive power and plasticity that allows easy modelling. This phenomenon is carbonation, according to the following reaction:

$$CaCO_3 + \text{thermal treatment} \rightarrow Ca(OH)_2 + CO_2 \rightarrow CaCO_3 + H_2O$$

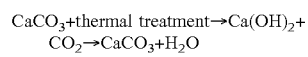

In this reaction, during which the temperature rises and is maintained for a time from 20 to 40 min, the calcium carbonate is transformed chemically into lime, then under the action of the $CO_2$ and ambient moisture it becomes amorphous calcium carbonate. This chemical transformation takes place over several days, depending on the ambient hygrometry.

Thus, the pulverulent semisynthetic material according to the invention comprises a powder derived from a natural marine material whose organic fraction is supplemented with extracted insoluble and soluble biopolymers, and the mineral fraction is supplemented with calcium carbonate of sedimentary or madrepore marine origin, or of sedimentary or precipitated terrestrial origin, transformed by a carbonation process.

According to a particular embodiment, the pulverulent semisynthetic material according to the invention comprises aragonite in pulverulent form with a granulometry from 5 nm to 100 μm, preferably from 20 nm to 50 μm, even more preferably from 50 nm to 20 μm, insoluble and soluble extracted biopolymers, and calcium carbonate transformed by carbonation.

By adding the insoluble and soluble extracted biopolymers, the proportion of the organic fraction of the initial material is increased in a range between 1% and 10%, preferably respecting the proportions between insoluble biopolymers and soluble biopolymers existing in the starting material. By adding calcium carbonate transformed by carbonation, the proportion of the mineral fraction of the initial material is increased in a range between 1% and 10%, depending on the desired physicochemical characteristics.

According to a particular embodiment, the semisynthetic material according to the invention comprises:
- for 100 g of aragonite in pulverulent form with a granulometry from 5 nm to 100 μm, preferably from 20 nm to 50 μm, even more preferably from 50 nm to 20 μm;
- from 1 g to 50 g, preferably from 5 g to 25 g, even more preferably from 10 g to 15 g of insoluble and soluble extracted biopolymers; and
- from 0.5 g to 50 g, preferably from 1 g to 25 g, even more preferably from 2 g to 10 g of calcium carbonate transformed by carbonation.

During extraction of the biopolymers, the inventors demonstrated that in the aragonitic inner layer and calcitic outer layer of the molluscs used for carrying out the invention, the proportion of the insoluble biopolymers represents from 2.6% to 4.3% and that of the soluble biopolymers from 0.4% to 0.7% of the total weight. Biopolymers are added to the material according to the invention in such a way that the ratio of soluble biopolymers to insoluble biopolymers is similar to the ratio in the original natural product.

The invention also relates to a method for preparing a pulverulent semisynthetic material, as described above.

According to the method of the invention, the constituent elements are prepared separately and then mixed so as to obtain the material according to the invention. Thus, the pulverulent material derived from a natural marine biomaterial, the insoluble and soluble biopolymers extracted from a natural marine biomaterial and the calcium carbonate transformed by carbonation are prepared.

More particularly, the method of preparation comprises mixing a ground natural biomaterial, insoluble and soluble polymers extracted from the aragonitic inner layer and/or from the calcitic outer layer of the shell of the bivalve molluscs selected from the group comprising Pinctadines, notably *Pinctada maxima, margaritifera*, and Tridacnes, notably *Tridacna gigas, maxima, derasa, tevaroa, squamosa, crocea, Hippopus hippopus, Hippopus porcelanus* and calcium carbonate transformed by carbonation.

In a particular embodiment, the ground natural biomaterial is the aragonitic inner layer of the shell of the molluscs. Grinding is carried out so as to obtain an average granulometry from 20 nm to 50 μm. The grains obtained may be spheronized to improve the flowability and compressibility of the powder.

In the method according to the invention, the insoluble and soluble biopolymers are extracted respectively by supercentrifugation and by tangential ultrafiltration coupled to reverse osmosis after hydrolysis. Before extraction, the aragonitic inner layer and/or the calcitic outer layer of the shell of the molluscs may be crosslinked. To facilitate extraction, the aragonitic inner layer and/or the calcitic outer layer of the shell of the molluscs is(are) ground and sieved to a granulometry between 250 μm and 50 μm.

These various steps are described successively hereunder.

The natural marine biomaterial used as raw material is selected from the group comprising Pinctadines, notably *Pinctada maxima, margaritifera*, and Tridacnes, notably *Tridacna gigas, maxima, derasa, tevaroa, squamosa, crocea, Hippopus hippopus, Hippopus porcelanus*.

Each of the components may be derived from the same marine biomaterial or from different marine biomaterials.

The shells selected are cleaned, decontaminated, optionally crosslinked, and the calcitic layer is separated from the inner layer. The inner layer is ground. A portion of the ground inner layer constitutes the base component of the material according to the invention. The soluble and insoluble biopolymers are extracted from the calcitic layer and/or from the inner layer. The calcium carbonate, which may be derived from the mineral portion recovered after extraction of the biopolymers, is transformed by carbonation. The biopolymers thus extracted and the calcium carbonate transformed by carbonation are added to the base component previously obtained.

A specific embodiment of the method according to the invention is described in detail hereunder. Of course, a person skilled in the art will be able to adapt the conditions of this method to the specific starting biomaterials and to the desired end uses.

I. Preparation of the Components

After removing the epibiont by scraping, the shells obtained from the selected marine biomaterial undergo the following treatments:

I.1) Decontamination of the Shells

The shells are decontaminated by immersing in a bath of mains water to which a solution of hypochlorite at 2% of active chlorine is added.

I.2) Ultrasonic Treatment of the Shells

The shells are then rinsed and treated with ultrasound in a tank filled with microbiologically inspected mains water, for example at a temperature of 55° C., to which a cleaning and disinfecting solution is added at a dilution of 1 part of solution to 127 parts of water. The treatment time is about 30 min at a frequency of about 40 kHz.

I.3) Rinsing and Drying the Shells

The shells are then rinsed for example for 20 min in a bath of demineralized water at a temperature of 90° C., to which Calbenium® is added at a dilution of 2%, for 30 min. They are then dried.

I.4) Crosslinking of the Shells

According to another embodiment, in order to endow the biomaterial of natural origin with enhanced biological properties, notably in view of the optimization of cellular metabolism and the reinforcement of the anti-radical properties, the shells may be crosslinked as follows:

In a translucent glass or plastic container of variable capacity, a mixture of mains water with addition of 10% riboflavin is prepared; the whole is maintained at a temperature above 20° C., and stirring of the mixture generates a flow perpendicular to the UVA radiation.

The shells are placed therein vertically and are submitted on both sides to irradiation from UVA lamps with a wavelength of 365 nanometers/second, at an intensity of 2300 microjoules per square centimeter for 180 min. The whole is kept under vacuum throughout the treatment.

The shells are then rinsed and dried in a stream of hot air at 40° C.

It is also possible to use the method described in patent application FR 14 50204 filed on 10 Jan. 2014.

I.5) Removal of the Calcitic Outer Layer

The calcitic outer layer of the shells is removed by grinding, with a fine-grain grinding wheel.

The product is put to one side and constitutes the "Batch for extraction of the biopolymers from the calcitic outer layer".

I.6) Freezing of the Nacreous Tests Exposed after Grinding

According to the invention, the nacreous tests are frozen at a temperature of −18° C. for 120 min.

I.7) Crushing of the Nacreous Tests and Recovery of the Batches

Then crushing of the nacreous tests is carried out for example in a crusher with tungsten carbide jaws, with aspiration, so as to recover the suspended particles, which also contain nano-grains.

The crushing operation is repeated at least 3 times, and 2 batches are set aside after sieving:
The first with a random granulometry from 20 microns to 50 nanometers will constitute the aragonite mixed portion of the product according to the invention, called "aragonite mixed batch" hereinafter. "Aragonite mixed batch" means the pulverulent form obtained after grinding, comprising the two organic and inorganic components.
The second batch with a granulometry from 250 to 50 microns is put to one side for extraction of the insoluble and soluble biopolymers. It will be called "batch for extraction of the biopolymers from the aragonitic inner layer".

A laser granulometer will be used for determining the grain size and size range of the powders obtained.

I.8) Spherification of the Aragonite Mixed Batch

The aragonite mixed batch undergoes mechanical treatment intended to make the grains uniform by spherification, the aim being to round off the corners and edges of the grains by attrition.

This treatment has the effect of promoting the flowability and compressibility of the powder obtained and thus promote densification and inter-particle bonds when using the material according to the invention, notably as bone substitutes, sealing cements, injectable cements, bioabsorbable osteosynthesis devices and moulded implants.

The following procedure may be adopted for this spherification step: A mixture of equal parts of pulverulent material from the aragonite mixed batch and chips of some mm² of hard wood, for example oak, sterilized in an autoclave, is put in a cylindrical container made of glass or zirconium for example, with horizon tal rotation axis, which has glass blades of variable width.

The container is rotated for a variable time and at a variable speed, depending on the size of the container and the amount of product to be treated.

At the end of the spherification treatment, the whole mixture, aragonite mixed batch and chips, is recovered in an inert container filled with a sufficient amount of water, which is stirred continuously for about 15 min. After resting, the wood chips floating on the surface are removed by suction.

The solution is then filtered on a nylon filter with mesh with a diameter of 20 microns, then the residue is dried in the Rotavapor® at 40° C. and packaged.

According to another embodiment, equal parts of sodium chloride in the form of grains with random diameters ranging from 1 to 3 mm may also be added to the aragonite mixed batch. After treatment, the sodium chloride is removed by dissolving with hot water at 90° C. and filtering on a nylon filter, followed by washing with hot water at 90° C. and drying in a stream of hot air at 40° C.

II. Extraction of the Biopolymers

II.1 Extraction of the Insoluble Biopolymers

According to the invention, a suitable amount of powder from the batch for extraction of the biopolymers from the aragonitic inner layer obtained in step 1.5) is mixed with a sufficient amount of demineralized water, to be injected into a hydrolysis reactor, to which a defined amount of 25% citric acid is added; the whole is cooled at a temperature fluctuating between 4 and 5° C., stirring continuously. The inventors favoured the use of citric acid owing to its properties of lowering the pH and surface tension.

The pH, monitored with a pH-meter, is maintained above 4.5 by adding 2.5 N sodium hydroxide to prevent degradation of the biopolymers; it is then brought back to 7 at the end of the step by adding 0.1 liter of 5N sodium hydroxide per 100 liters of hydrolysate.

Once the powder has dissolved completely, the hydrolysate is transferred to a storage tank, still stirring continuously, and is then transferred to a centrifugal separator, where it is subjected to a force of from 18 to 20 000 G in the cyclone.

The operation is repeated if necessary after checking the solution by turbidimetry and correcting with citric acid if necessary, while maintaining the temperature between 4 and 5° C.

Depending on the results from turbidimetry, the hydrolysate may undergo supercentrifugation again.

At each cycle of supercentrifugation, the residue of the insoluble biopolymers collected is washed and set aside. The water from washing the residues is treated with oxalic acid to check for presence or absence of calcium.

At the end of the last supercentrifugation, a residue is therefore obtained containing all the insoluble biopolymers, in the form of a wet brownish cake, which is dried by lyophilization, or Zeodratation (hydration using zeolites); at the end of treatment we have grey spherules with diameter from 2 to 3 mm, resulting from the coiling of the proteins under the action of the centrifugal force.

The insoluble biopolymers extracted are ground for example in a planetary mill until a powder is obtained with a random granulometry from 5 microns to 100 nanometers, recovered after sieving.

II.2 Extraction of the Soluble Biopolymers

The permeate and the wash water are sent for desalting in a tangential ultrafiltration device, for example with cassettes having a cut-off point of 1 kD.

A sufficient amount of sulphuric acid at 2.0 mol/L is added to the permeate, in order to cause precipitation of the calcium sulphate salts.

The solution is filtered, and the permeate is concentrated in the Rotavapor® under vacuum at a boiling point of 33° C. in order to remove the citric acid in the form of crystals.

The distillate containing the low molecular weight proteins as well as the mono- and multivalent ions is extended.

As the cut-off point of the cassettes does not retain all of the proteins and notably those of very low molecular weight, the distillate is submitted to reverse osmosis.

The distillate is transferred to undergo a liquid-phase separation treatment by permeation through semi-selective membranes for example with a pore diameter of 0.0001 micron, under the effect of a pressure gradient from 40 to 80 bar.

The distillate is passed so as to retain all the mono- and multivalent ions such as iron, magnesium, zinc, etc.

The retentate recovered on the reverse osmosis membranes is collected and extended with apyrogenic water, then concentrated for example in the Rotavapor®, under vacuum, at a temperature of 40° C., and then lyophilized by Zeodratation or cryodessication.

A very fine greyish-white powder is obtained, which is put to one side, and then ground for example in a planetary mill to obtain, after sieving, a powder with random granulometry ranging from 5 microns to 100 nanometers.

The permeate is checked for presence or absence of proteins by taking an aliquot of solution, which is treated by Bradford's colorimetric method.

II.3 Extraction of the Biopolymers from the Batch for Extraction of Biopolymers from the Calcitic Outer Layer According to another embodiment, extraction of the biopolymers from the calcitic outer layer is carried out identically to that of the biopolymers from the aragonitic inner layer.

III. Carbonation of Calcium Carbonate

It is known that calcium carbonate, crystallized in the orthorhombic or rhombohedral system, when submitted to thermal treatment between 800 and 1100° C., presents novel properties through thermolysis and oxidation, which are reflected in considerable adhesive power and plasticity that allows easy modelling. This phenomenon is carbonation, according to the following reaction:

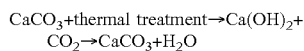
$CaCO_3$+thermal treatment→$Ca(OH)_2$+ $CO_2$→$CaCO_3$+$H_2O$

In this reaction, during which the temperature rises and is maintained for a time of from 20 to 40 min, the calcium carbonate is transformed chemically, becoming lime, and then under the action of the $CO_2$ and ambient moisture, it becomes amorphous calcium carbonate. This chemical transformation takes place over several days, depending on the ambient hygrometry.

According to other embodiments, all the calcium salts, other than calcium carbonate, may, by chemical reactions of precipitation, give rise to calcium carbonate, which can be transformed by carbonation. Thus, it is possible, for example, to obtain carbonated calcium carbonate starting from calcium hydroxide, calcium acetate, calcium oxalate, calcium sulphate, or calcium citrate; it is within the skill set of a person skilled in the art to carry out the known chemical processes for these precipitations.

The calcium carbonate may also come from the aragonitic inner shell of the bivalve molluscs such as the Pinctadines in general and notably *Pinctada maxima, margaritifera*, and the Tridacnes, *Tridacna gigas, maxima, derasa, tevaroa, squamosa, crocea, Hippopus hippopus, Hippopus porcelanus*, after extraction of the biopolymers. It may also be of madrepore origin.

IV. Formulation of a Mixture Starting from the Aragonite Mixed Batch, the Insoluble and Soluble Extracted Biopolymers, and Calcium Carbonate Transformed by Carbonation An amount of the insoluble and soluble biopolymers, extracted from two inner aragonite and outer calcite batches, determined according to the desired proportion of organic fraction, and a determined amount of calcium carbonate transformed by carbonation, are mixed with a defined amount of the aragonite mixed batch to constitute a formulation of the product according to the invention.

Mixing is carried out for example in a knife mixer until a homogeneous powder is obtained, which is then packaged.

According to another aspect, the invention relates to the use of the material according to the invention as bone substitute for extemporaneous formulation, for healing and regeneration of losses of substance, for treating burns, sores, ulcers, erythematous skin lesions or in the manufacture of devices or moulded implants.

The pulverulent semisynthetic material according to the invention may also be used in the manufacture of devices or moulded implants with controlled bioabsorption comprising suture threads with bioabsorption staggered over time.

It may also be used for formulating preparations for bone substitutes for extemporaneous use, bone substitutes with porous collagen support, bone substitutes with a mineral structure of animal or human origin, bioabsorbable osteosynthesis devices and moulded implants, devices with controlled bioabsorption, cements for sealing endoprostheses, injectable cements for minimally invasive surgery in vertebroplasty, kyphoplasty and bone tumour surgery.

According to another embodiment, the product according to the invention may be combined with a porous collagen support such as Spongia officinalis that has undergone mechanical and thermochemical treatment intended for bacterial and viral decontamination, for removal of any pigments, and for neutralizing immunogenicity. It is known that Spongia officinalis is made up of spongin, consisting in its turn of fibres of a carbonated scleroprotein related to collagen. This protein is of low solubility and plays a role of protection and support of all tissues: connective tissue, tendons, bone tissues, muscle fibres, skin, hair and nails. Spongin is a structural and storage collagen protein; it is inert, water-insoluble, hydrophobic and is not easily denatured. It constitutes a porous support, suitable for osteoconduction. It may therefore be used in combination with the material according to the invention for making bone substitutes.

The material according to the invention may be combined with calcium salts such as dehydrated or hemi-hydrated calcium sulphate, calcite, anhydrous calcium hydroxyphosphate, β-TCP, and calcium hydroxide. The material according to the invention may be combined with mineral structures of bone tissues of animal or human origin.

It may also be combined with bioabsorbable polymers such as collagen, hyaluronic acid, chitosan, starch, alginate or with absorbable synthetic polymers such as polyglycolide, poly(DL-lactide-co-glycolide), poly(L-lactide) or with acrylic polymers such as polyhydroxyethyl, methylmethacrylate, polymethylmethacrylate, as well as with medicinal substances in pulverulent form, such as non-steroidal anti-inflammatory drugs, antibiotics, antimitotics or any other substance with a therapeutic objective.

Taking into account the drawbacks connected with the use of methylmethacrylate sealing cements, the inventors propose sealing cements manufactured with the product according to the invention, which, being naturally radiopaque, performs mechanical primary retention of the endoprosthesis on account of its adhesive properties, leading secondly to tissue integration by reason of its osteomimetic, osteoinductive, osteoconductive, and bioactive properties, induced by the presence of signal molecules, initiators of biomineralization.

These signal molecules stimulate the local endogenous factors of biomineralization in situ, leading to the formation of metaplastic bone.

According to another aim, the invention relates to the use of calcium carbonate that has undergone carbonation as employed in the material according to the invention or as prepared according to step III of the method described above in compositions comprising calcium salts, natural or synthetic polymers, collagen, mineral structures of bone tissues of animal or human origin.

It may also be combined with bioabsorbable polymers such as collagen, hyaluronic acid, chitosan, starch, alginate or with absorbable synthetic polymers such as polyglycolide, poly(DL-lactide-co-glycolide), poly(L-lactide) or with acrylic polymers such as polyhydroxyethyl, methylmethacrylate, polymethylmethacrylate, as well as with medicinal substances in pulverulent form, such as non-steroidal anti-inflammatory drugs, antibiotics, antimitotics or any other substance with a therapeutic objective.

It is known that the insoluble and soluble biopolymers contained in the organic fraction of the aragonitic and calcitic layers have healing and regeneration properties, both of hard tissues such as bone and cartilage, and soft tissues such as the skin, muscles and mucosae. Certain of these non-collagen biopolymers, notably the low molecular weight glycoproteins, may be likened to growth factors such as BMP, TNFβ, EGPF, TGFβ, IGF, FGF, etc., as well as cytokines, mediators of inflammation.

The invention also relates to the use of the soluble and insoluble biopolymers employed in the material according to the invention or as extracted by step II of the method described above as additives for pulverulent compositions comprising calcium salts, natural or synthetic polymers, collagen, mineral structures of bone tissues of animal or human origin. They may also be combined with bioabsorbable polymers such as collagen, hyaluronic acid, chitosan, starch, alginate or with absorbable synthetic polymers such as polyglycolide, poly(DL-lactide-co-glycolide), poly(L-lactide) or with acrylic polymers such as polyhydroxyethyl, methylmethacrylate, polymethylmethacrylate, as well as with medicinal substances in pulverulent form, such as non-steroidal anti-inflammatory drugs, antibiotics, antimitotics or any other substance with a therapeutic objective. They may also be combined with calcium carbonate transformed by carbonation.

Figure 2:
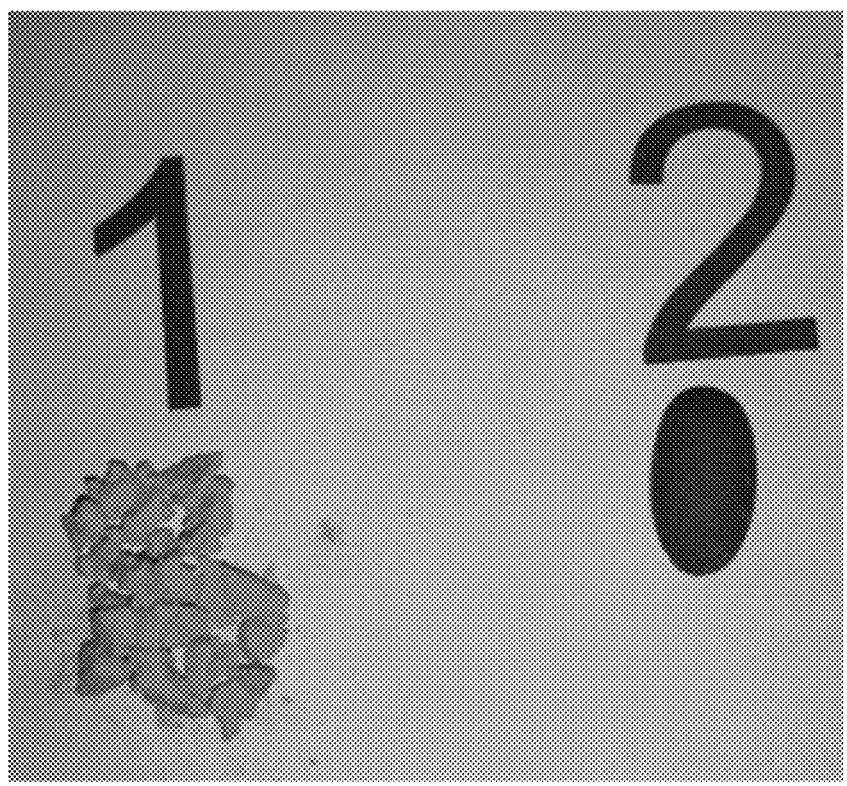

The invention will be described in more detail with the aid of the following examples, given purely for illustration, and the appended drawings, where:

FIG. 1 and FIG. 2 are photographs of mixtures:
of powder of nacre and calcium carbonate with whole blood (No. 1) and
of powder of nacre and calcium carbonate that has undergone carbonation with whole blood (No. 2)

taken respectively 2 min and then 15 min after adding the whole blood.

EXAMPLES

In order to verify the pharmacological properties of the product according to the invention, the inventors formulated preparations with a therapeutic objective and used them for recording clinical observations.

Example 1

The pulverulent semisynthetic material according to the invention was prepared as follows:

I. Preparation of the Components

After removing the epibiont by scraping, the shells undergo the following treatments:

I.1) Decontamination of the Shells

The shells are decontaminated by immersing in a bath of mains water to which a solution of hypochlorite at 2% of active chlorine has been added.

I.2) Ultrasonic Treatment of the Shells

The shells are then rinsed and treated with ultrasound in a tank filled with microbiologically inspected mains water, at a temperature of 55° C., to which a cleaning and disinfecting solution is added at a dilution of 1 part of solution to 127 parts of water. The treatment time is 30 min at a frequency of 40 kHz.

I.3) Rinsing and Drying of the Shells

The shells are then rinsed for 20 min in a bath of demineralized water at a temperature of 90° C., with Calbenium® added at a dilution of 2%, for 30 min. They are then rinsed and dried.

I.4) Removal of the Calcitic Outer Layer

The calcitic outer layer of the shells is removed by grinding, with a fine-grain grinding wheel.
The product is put to one side and constitutes the "Batch for extraction of the biopolymers from the calcitic outer layer".

I.5) Freezing of the Nacreous Tests Exposed after Grinding

The nacreous tests obtained in step I.4) are frozen at a temperature of −18° C. for 120 min.

I.6) Crushing of the Nacreous Tests and Recovery of the Batches

Then the nacreous tests are crushed in a crusher with tungsten carbide jaws, of the ESSA® type, with aspiration, so as to recover the suspended particles, also containing nano-grains.
The crushing operation is repeated at least 3 times and 2 batches are put aside after sieving:
The first with a random granulometry from 20 microns to 50 nanometers will constitute the aragonite mixed portion of the product according to the invention called "aragonite mixed batch" hereinafter. "Aragonite mixed batch" means the pulverulent form obtained after grinding, comprising the two organic and inorganic components.

The second batch with a granulometry from 250 to 50 microns is put to one side for extraction of the insoluble and soluble biopolymers. It will be called "batch for extraction of the biopolymers from the aragonite inner layer".

The grain size and range of the powders obtained are determined using a laser granulometer.

I.7) Spherification of the Aragonite Mixed Batch

The aragonite mixed batch undergoes mechanical treatment that is intended to make the grains uniform by spherification, the aim being to round off the corners and edges of the grains by attrition.

A mixture of equal parts of pulverulent material from the aragonite mixed batch and 5 mm² chips of hard wood, for example oak, sterilized in the autoclave, is put in a cylindrical container made of zirconium, with horizontal rotation axis, which has glass blades of variable width.

The container is rotated for a variable time and at a variable speed, depending on the size of the container and the amount of product to be treated.

At the end of the spherification treatment, the whole mixture, aragonite mixed batch and chips, is recovered in an inert container filled with a sufficient amount of water, which is stirred continuously for 15 min. After a 30 min rest, the wood chips floating on the surface are removed by suction.

The solution is then filtered on a nylon filter with mesh having a diameter of 20 microns, then the residue is dried in the Rotavapor® at 40° C. and packaged.

II. Extraction of the Biopolymers

II.1 Extraction of the Insoluble Biopolymers

A suitable amount of powder from the batch for extraction of the biopolymers from the aragonitic inner layer is mixed, by aspiration in the feed tank in Zone I, with a sufficient amount of demineralized water, to be injected in Zone II into the hydrolysis reactor, to which a defined amount of 25% citric acid is added; the whole is cooled at a temperature fluctuating between 4 and 5° C., stirring continuously. The pH, monitored with a pH-meter, is maintained above 4.5 by adding 2.5 N sodium hydroxide to prevent degradation of the biopolymers; it is then brought back to 7 at the end of the step by adding 0.1 liter of 5N sodium hydroxide per 100 liters of hydrolysate.

Once the powder has dissolved completely, the hydrolysate is transferred to the storage tank, still stirring continuously, then transferred to the centrifugal separator, where it is submitted to a force from 18 to 20 000 G in the cyclone.

The operation is repeated if necessary after checking the solution by turbidimetry and correcting with citric acid if necessary, the temperature being maintained between 4 and 5° C.

Depending on the results supplied by turbidimetry, the hydrolysate undergoes supercentrifugation again.

In each cycle of supercentrifugation, the residue of the insoluble biopolymers collected is washed and set aside. The water from washing the residues is treated with oxalic acid to check for presence or absence of calcium.

At the end of the last supercentrifugation, a residue is therefore obtained containing all the insoluble biopolymers, in the form of a wet brownish cake, which is dried by lyophilization, and at the end of treatment we have grey spherules with a diameter from 2 to 3 mm, resulting from the coiling of the proteins under the action of the centrifugal force.

The insoluble biopolymers extracted are ground in a planetary mill until a powder is obtained with a random granulometry from 5 microns to 100 nanometers, which is recovered after sieving.

II.2 Extraction of the Soluble Biopolymers

The permeate and the wash water are sent for desalting in the device for assembly of the tangential ultrafiltration cassettes, Millipore® of 1 kDa each, mounted in series to give a surface area of 15 m², at a pressure of 5 bar and a flow rate from 10 to 15 liters per hour, at a temperature of 40° C.

A sufficient amount of sulphuric acid at 2.0 mol/L is added to the permeate, to cause precipitation of the calcium sulphate salts.

The solution is filtered, the permeate is concentrated in the Rotavapor® under vacuum at a boiling point of 33° C. in order to remove the citric acid in the form of crystals.

The distillate containing the low molecular weight proteins as well as the mono- and multivalent ions is extended.

As the cut-off point of the cassettes does not retain all of the proteins and notably those of very low molecular weight, the distillate is submitted to reverse osmosis.

The distillate is then transferred to undergo a liquid-phase separation treatment by permeation through semi-selective membranes with membrane pore diameter of 0.0001 micron, under the effect of a pressure gradient from 40 to 80 bar.

The distillate is passed in order to retain all the mono- and multivalent ions such as iron, magnesium, zinc, etc.

The retentate recovered on the reverse osmosis membranes is collected and extended with apyrogenic water, then concentrated in the Rotavapor®, under vacuum, at a temperature of 40° C., and then lyophilized by Zeodratation.

A very fine greyish-white powder is obtained, which is put to one side, and is then ground in a planetary mill, obtaining, after sieving, a powder with random granulometry ranging from 5 microns to 100 nanometers.

Presence or absence of proteins in the permeate is checked by taking an aliquot of solution, which is treated by Bradford's colorimetric method.

III. Carbonation of the Calcium Carbonate

The calcium carbonate recovered after extraction of the above biopolymers is submitted to thermal treatment between 800 and 1100° C., lasting 20 to 40 min, then cooled slowly in the open air. This phenomenon is carbonation, according to the following reaction:

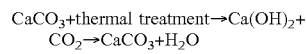

$$CaCO_3 + \text{thermal treatment} \rightarrow Ca(OH)_2 + CO_2 \rightarrow CaCO_3 + H_2O$$

In this reaction, the calcium carbonate is transformed chemically, becoming lime, and then under the action of $CO_2$ and humidity it becomes amorphous calcium carbonate again. This chemical transformation takes place over several days, depending on the ambient hygrometry.

IV. Formulation of a Mixture Starting from the Aragonite Mixed Batch, the Insoluble and Soluble Extracted Biopolymers, and the Calcium Carbonate Transformed by Carbonation During extraction of the biopolymers, it was demonstrated that in the aragonitic inner layer and the calcitic outer layer of the shells used, the proportion of the insoluble biopolymers represented from 2.6% to 4.3% and that of the soluble biopolymers represented from 0.4% to 0.7%.

The material according to the invention was prepared by mixing the aragonite mixed batch, insoluble polymers obtained in step II.1, soluble polymers obtained in step II.2 and calcium carbonate that has undergone carbonation obtained in step III above. The specific amounts of the various components are specified in each of the embodiment examples given below.

Mixing is carried out in a knife mixer until a homogeneous powder is obtained, which is then packaged.

Example 2

The procedure of example 1 above is followed, except that a crosslinking step as described below is added at the end of step 1.3.

A mixture of mains water with 10% riboflavin added is prepared in a translucent glass or plastic container; the whole is maintained at a temperature above 20° C., and stirring of the mixture generates a flow perpendicular to the UVA radiation.
The shells are placed vertically therein and are subjected on both sides to irradiation with UVA lamps with a wavelength of 365 nanometers/second, at an intensity of 2300 microjoules per square centimeter for 180 min. The whole is kept under vacuum throughout the treatment.

The shells are then rinsed and dried in a stream of hot air at 40° C.

Example 3

The properties of adhesiveness and cohesion of the carbonated calcium carbonate are verified as follows:

To two Dappen cups, designated Dappen No. 1 and No. 2 respectively, each containing 1 g of the powdered nacre obtained at the end of step I.7 of the procedure in example 1, the following are added:
  0.1 g of natural calcium carbonate (Dappen No. 1),
  0.1 g of natural calcium carbonate that has undergone carbonation, obtained from step III of the procedure of example 1 (Dappen No. 2).

After mixing, the contents of each Dappen cup are mixed with 2 cc of whole blood.

A photograph of each Dappen cup is taken 2 minutes (FIG. 1) and then 15 minutes (FIG. 2) after mixing with whole blood.

As illustrated in FIG. 1(1), the mixture in Dappen No. 1 remains in the form of a red powder; no coagulum has formed. After 15 minutes, no coagulum has formed (FIG. 2(1)).

As illustrated in FIG. 1(2), the mixture in Dappen No. 2 quickly forms a coagulum and gradually changes colour from red to brown, it cakes, can be modelled, becomes sticky and hardens after 15 minutes (FIG. 2(2)).

Example 4: Formulation for Extemporaneous Bone Substitute

A critical clinical case was an oblique fracture of the cannon of a 1-year-old filly, treated by osteosynthesis. After osteosynthesis failed, reflected in breakage of 4 screws, pseudarthrosis with sepsis, followed by a comminuted secondary fracture with small fragments, leaving euthanasia of the animal as the only alternative, it was decided to use the material according to the invention with the following formulation:
  40 g of aragonite mixed batch with a granulometry from 50 nanometers to 20 microns, resulting from step I.8 of example 1;
  0.070 g of insoluble extracted biopolymers obtained in step 11.2 of example 1;
  0.010 g of soluble extracted biopolymers obtained in step II.1 of example 1;
  2 g of carbonated calcium carbonate resulting from step III of the procedure of example 1;
  10 ml of autologous venous blood to form a coagulum, modelled into the shape of a cylinder with length of 10 cm and diameter of 2 cm, placed in the loss of substance after ablation of the bone sequestra.

The limb, protected with compresses, was put in plaster. Post-operative radiography showed the presence and adhesion of the bone substitute according to the invention, then consolidation at 4 months, after which the filly was able to gallop and jump obstacles. Later X-rays showed complete restoration of the bone shaft with reconstruction of the medullary canal.

The same formulation was also used, making a coagulum extemporaneously with 2.5 ml of water for injection (WFI) at room temperature.

Example 5: Formulation of a Skin Healing Cream

A preparation of the product according to the invention was made with the following percentage formulation:
  10 g of aragonite mixed batch with a granulometry from 50 nanometers to 20 microns obtained according to example 2;
  0.035 g of insoluble extracted biopolymers obtained in step 11.2 of example 1;
  0.005 g of soluble extracted biopolymers obtained in step II.1 of example 1;
  0.5 g of carbonated calcium carbonate;
  15 drops of a complex of essential oils comprising, for 100 ml:
    Lavandula spica: 1 ml
    Salvia officinalis: 2 ml
    Rosa rubiginosa: 10 ml
    Helichrysum italicum: 1.5 ml
    Wheatgerm vegetable oil: 50 ml
    Evening primrose oil: 10 ml
    Sweet almond oil: 20 ml
    O/W Emulsion, q.s. 100 g This preparation was applied on a cutaneous necrosis of the sternal plastron of a horse, from the base of the neck to the stifles, to a height of 32 cm and a width of 18 cm. Clinical observation showed exceptional healing of 1 cm per day in height and in width with reconstruction of the various aponeurotic, subcutaneous and cutaneous planes, and simultaneous regrowth of the hair without discoloration, with complete healing of the integuments in 28 days.

Example 6: Formulation for a Dermatological Preparation for Treating Psoriasis

As is well known, psoriasis is an inflammatory disorder of the skin, characterized by accelerated cell renewal, without apoptosis, which leads to the formation of thick crusts as plaques. Apart from corticosteroid therapy and local treatments based on coal tar and PUVA therapy, the results of which are variable and disappointing, there are more drastic treatments with dangerous side-effects for the patient.

A preparation of the product according to the invention is made according to the following percentage formulation:
- 3 g of insoluble extracted biopolymers obtained in step 11.2 of example 1;
- 0.45 g of soluble extracted biopolymers obtained in step II.1 of example 1;
- 0.5 g of carbonated calcium carbonate obtained in step III of example 1;
- 10 drops of a complex of essential oils containing, for 100 ml:
    - Lavandula spica: 1 ml
    - Salvia officinalis: 2 ml
    - Rosa rubiginosa: 10 ml
    - Helichrysum italicum: 1.5 ml
    - Wheatgerm vegetable oil: 50 ml
    - Evening primrose oil: 10 ml
    - Sweet almond oil: 20 ml
    - O/W Emulsion, q.s. 100 g This emulsion is applied daily on the lesions of severe psoriasis at the level of the torso, back, arms and legs. After the third application, disappearance of the redness is observed, indicating relief of the inflammatory phenomenon, skin flakes, and relief of pruritus and superimposed infections with a notable improvement in appearance. Improvement of the clinical signs reflects the eutrophic, antiphlogistic and regenerative properties of the insoluble and soluble biopolymers.

Example 7: Formulation of a Skin Dressing for Burns

The exceptional properties of soft tissue regeneration of the insoluble and soluble biopolymers extracted according to step II of example 1 were demonstrated in a case of deep second-degree and third-degree burns after failure of keratinocyte grafts, with the following formulation:

For 100 g:
- 50 g of aragonite mixed batch with a granulometry from 50 nanometers to 20 microns obtained according to example 2;
- 0.174 g of insoluble extracted biopolymers obtained in step 11.2 of example 1;
- 0.026 g of soluble extracted biopolymers obtained in step II.1 of example 1;
- Cérat de Galien (Galen's Wax) with cherry laurel water q.s. 100 g.

The preparation is applied on all of the burned areas under an occlusive dressing, and this is repeated every 72 hours.

Repeated clinical examinations have shown relief of the exudative phenomenon, significant angiogenesis, pain relief, re-epithelialization of the areas impregnated of blood and a notable decrease in fibroplastic strain.

Example 8: Formulation for Bioabsorbable Moulded Bone Substitute

The material according to the invention can be used for making bioabsorbable osteosynthesis devices and moulded implants.

According to the invention, the following is prepared, for 100 g:
- 80 g of aragonite mixed batch with a granulometry from 50 nanometers to 20 microns obtained in step 1.8 of example 1;
- 0.139 g of insoluble extracted biopolymers obtained in step 11.2 of example 1;
- 0.021 g of soluble extracted biopolymers obtained in step II.1 of example 1;
- 20 g of macrogol 400;
- 4 g of carbonated calcium carbonate obtained in step III of example 1.

The whole is mixed in a mixer for 10 min at room temperature until a homogeneous plastic paste is obtained that is extrudable and mouldable.

Mould cavities of suitable shape are produced by digital modelling of the anatomy of the possible zones for insertion of the osteosynthesis devices and/or implants.

A sufficient amount of the paste obtained previously is injected into the compression chamber of a mould comprising one or more mould cavities.

The whole is then compressed at a pressure gradually increasing from 100 to 220 N; the pressure is maintained for a variable time, gradually decreasing to 0.

The device, once removed from the mould and dried at 40° C., and packed in double packaging, is sterilized with ionizing radiation at 25 kGy.

Example 9: Preparation for Bone Substitute with Controlled Bioabsorbability

It has been found that the bioabsorption of a bone substitute, or of a bioabsorbable device, is directly linked to the diameters of the interconnected pores, which must vary from 5 to 100 microns, to allow its colonization by neovascularization and the cells involved in bone remodelling.

That is why the inventors propose making bone substitutes or moulded implants with controlled interconnected porosity.

For this purpose, the following preparation is made, for 100 g:
- 80 g of aragonite mixed batch with a granulometry from 50 nanometers to 20 microns obtained in example 2;
- 0.139 g of insoluble extracted biopolymers obtained in step 11.2 of example 1;
- 0.021 g of soluble extracted biopolymers obtained in step II.1 of example 1;
- 20 ml of a 50% solution of hydroxypropylmethylcellulose (HPMC);
- 20 mm$^3$ of strands of absorbable synthetic mono-filament suture threads, with length of 5 mm, with diameter ranging from 5/0 to 12/0.

These absorbable threads are polymers such as glycolic acid, glycolic copolymer, ε-caprolactone polyglactin (Vicryl Rapide or irradiated), chitosan. These threads display staggered absorption from 12 to 90 days.

As in the preceding example, the paste is injected into the cavities of a mould, and then compressed. The devices or implants are then removed from the mould, dried, packed in double packaging and sterilized as before at 25 kGy.

Example 10: Preparation for Injectable Bone Substitute and Endoprosthesis Sealing Cement Cements are prepared with the following composition, for 100 g:
- 80 g of the material according to the invention, consisting of:
- 73 g of aragonite mixed batch with a granulometry from 50 nanometers to 20 microns obtained at the end of step 1.8;

2.702 g of insoluble extracted biopolymers obtained in step 11.2 of example 1;
0.405 g of soluble extracted biopolymers obtained in step II.1 of example 1;
3.699 g of carbonated calcium carbonate resulting from step III of example 1;
20 g of HPMC in high-viscosity aqueous solution at 50%.

The product thus obtained is packaged under vacuum or under controlled atmosphere in syringes of variable capacity, from 0.5 cm³ to 1 cm³ for example, with straight or angled tips, stored cold at a temperature of about 4° C.

This preparation, also usable as sealing cement, makes it possible to avoid passage of the sealing product into the circulatory system, for example during sealing of the tail of the prosthesis in the medullary cavity.

Moreover, owing to its composition, it does not cause release of volatile substances with risk of impacting the pulmonary system.

Such a composition is also proposed for vertebroplasty and kyphoplasty in minimally invasive surgery.

Example 11: Preparation for Bone Substitute with Collagen Support

Bone substitutes are made with the following composition:
Preparation for 100 g:
50 g of aragonite mixed batch with a granulometry from 50 nanometers to 20 microns obtained in step 1.8 of example 1;
0.087 g of insoluble extracted biopolymers obtained in step 11.2 of example 1;
0.013 g of soluble extracted biopolymers obtained in step II.1 of example 1;
2.5 g of carbonated calcium carbonate obtained in step III of example 1;
50 g of macrogol 400.

The whole is mixed until a gel with a viscosity of about 10 Pa·s is obtained.

30 g of Spongia officinalis reduced to fragments with a size of 2 mm is added to this gel.

The whole is mixed until a homogeneous paste is obtained with a viscosity of about $10^8$ Pa·s. The whole is injected into a mould comprising mould cavities for osteosynthesis devices or implants. After mould release, the devices or implants are dried under a stream of hot air at 40° C., packed in double packaging and sterilized in accordance with the current protocol.

Example 12: Preparation for Bone Substitute

According to another embodiment, the biopolymers extracted from the aragonite fraction alone and/or from the calcite fraction may be added to any other biomaterial of synthetic or natural origin in order to optimize or induce certain properties, notably osteoinductive or osteomimetic properties that they lack.

Thus, osteoconductive substitutes, such as certain calcium salts, were supplemented with the biopolymers extracted from the aragonitic layer, according to the formulation for 100 g:
95 g of granules of βTCP, with granulometry ranging from 50 to 250 microns;
4.4 g of insoluble extracted biopolymers obtained in step 11.2 of example 1;
0.6 g of soluble extracted biopolymers obtained in step II.1 of example 1.

This preparation, mixed with autologous blood, is inserted in a bone defect created by the exeresis of a cyst at the apex of the upper central incisor.

At the same time, βTCP alone is compacted in a loss of substance created by the exeresis of a periapical granuloma at the upper canine.

Radiological examination performed at 2 weeks showed greater and quicker bone densification in the cyst cavity treated with the mixture βTCP+insoluble and soluble extracted biopolymers than in the second cavity, in which the granules of βTCP are apparent, where only osteoconduction is expressed, whereas in the cyst cavity, osteoinduction is concomitant with osteoconduction, indicating that the βTCP has acquired a novel property.

The invention claimed is:

1. A method for preparing a pulverulent semisynthetic material, comprising the steps of:
grinding an aragonitic inner layer of a shell from a bivalve mollusc selected from the group consisting of Pinctadines and Tridacnes to obtain a ground natural biomaterial;
extracting insoluble and soluble polymers from at least one source selected from the group consisting of (i) a portion of the ground natural biomaterial and (ii) a calcitic outer layer of a shell from a bivalve mollusc selected from the group consisting of Pinctadines and Tridacnes, said extracting comprising the steps of
hydrolysing the at least one source by dissolving the at least one source in an aqueous solution of citric acid having a pH of about 4.5 or greater to form a hydrolysate solution,
subjecting the hydrolysate solution to supercentrifugation at a force of 18 to 20,000 G to obtain a supercentrifugation retentate and a supercentrifugation permeate, said supercentrifugation retentate being the insoluble polymers,
subjecting the permeate with added sulfuric acid to tangential ultrafiltration with a cut-off of 1 kDa to obtain a tangential ultrafiltration retentate and a tangential ultrafiltration permeate, said tangential ultrafiltration permeate being a first portion of soluble polymers,
subjecting the tangential ultrafiltration retentate to concentration under vacuum to obtain a distillate, and
subjecting the distillate to filtration by reverse osmosis to obtain a reverse osmosis retentate, said reverse osmosis retentate being a second portion of soluble polymers;
heating calcium carbonate between 800° C. to 1100° C. for 20 min to 40 min to obtain a calcium carbonate transformed by carbonation; and
mixing the ground natural biomaterial or a remaining portion of the ground natural biomaterial, the insoluble polymers, the first and the second portions of the soluble polymers, and the calcium carbonate transformed by carbonation to obtain the pulverulent semisynthetic material.

2. The method according to claim 1, wherein the insoluble and soluble polymers are extracted from the portion of the ground natural biomaterial, and the method further comprises, before the step of extracting the insoluble and soluble polymers, a step of sieving the ground natural biomaterial to a granulometry between 250 μm and 50 μm.

3. The method according to claim 1, wherein the insoluble and soluble polymers are extracted from the calcitic outer layer, and the method further comprises, before the step of extracting the insoluble and soluble polymers, the steps of:

grinding the calcitic outer layer to obtain a ground calcitic outer layer, and sieving the ground calcitic outer layer to a granulometry between 250 µm and 50 µm.

4. The method according to claim 1, wherein the insoluble and soluble polymers are extracted from the portion of ground natural biomaterial and the calcitic outer layer, and the method further comprises, before the step of extracting the insoluble and soluble polymers, the steps of:

sieving the ground natural biomaterial to a granulometry between 250 µm and 50 µm, grinding the calcitic outer layer to obtain a ground calcitic outer layer, and sieving the ground calcitic outer layer to a granulometry between 250 µm and 50 µm.

5. The method according to claim 1, wherein the Pinctadines are selected from the group consisting of *Pinctada maxima* and *Pinctada margaritifera*.

6. The method according to claim 1, wherein the Tridacnes are selected from the group consisting of *Tridacna gigas, Tridacna maxima, Tridacna derasa, Tridacna tevaroa, Tridacna squamosa, Tridacna crocea, Hippopus hippopus,* and *Hippopus porcelanus*.

7. The method according to claim 1, wherein the step of hydrolysing is performed under continuous stirring with the aqueous solution comprising citric acid at a temperature between 4 and 5° C.

* * * * *